(12) United States Patent
Ernst et al.

(10) Patent No.: US 7,482,338 B2
(45) Date of Patent: Jan. 27, 2009

(54) NON-AMIDE NONANES

(75) Inventors: Glen Ernst, Wilmington, DE (US);
Eifion Phillips, Boothwyn, PA (US);
Richard J Schmiesing, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/573,132

(22) PCT Filed: Sep. 24, 2004

(86) PCT No.: PCT/GB2004/004130

§ 371 (c)(1),
(2), (4) Date: Oct. 23, 2006

(87) PCT Pub. No.: WO2005/030777

PCT Pub. Date: Apr. 7, 2005

(65) Prior Publication Data

US 2007/0043031 A1    Feb. 22, 2007

Related U.S. Application Data

(60) Provisional application No. 60/506,664, filed on Sep. 26, 2003.

(51) Int. Cl.
*A01N 43/62* (2006.01)
*A61K 31/55* (2006.01)
*C07D 243/00* (2006.01)
*C07D 487/00* (2006.01)
*C07D 491/00* (2006.01)
*C07D 513/00* (2006.01)
*C07D 515/00* (2006.01)

(52) U.S. Cl. ...................... 514/221; 540/556

(58) Field of Classification Search .................. None
See application file for complete search history.

(56) References Cited

U.S. PATENT DOCUMENTS 5,679,673 A * 10/1997 Bowen et al. .............. 514/221
6,407,095 B1    6/2002 Lochead et al.
6,844,337 B2 *  1/2005 Galli et al. ................ 514/221

FOREIGN PATENT DOCUMENTS

EP    0 366 301 A2    5/1990
EP    1 219 622 A2    7/2002

OTHER PUBLICATIONS

International Search Report, Jan. 31, 2005.
* cited by examiner

*Primary Examiner*—James O. Wilson
*Assistant Examiner*—Jeffrey H Murray
(74) *Attorney, Agent, or Firm*—Kenneth F. Mitchell; Michael A. Patané

(57) ABSTRACT

Compounds of Formula I:

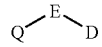

and pharmaceutically-acceptable salts thereof, wherein Q, E and D are as defined in the specification, enantiomers, in vivo-hydrolysable precursors, pharmaceutical compositions and formulations containing them, methods of using them to treat diseases and conditions either alone or in combination with other therapeutically-active compounds or substances, processes and intermediates used to prepare them and uses of them for diagnostic and analytic purposes.

4 Claims, No Drawings

NON-AMIDE NONANES

RELATED APPLICATIONS

This is a National Phase Application of PCT/GB2004/004130, filed Sep. 24, 2004, which claims the priority of U.S. Provisional Application 60/506,664 filed Sep. 26, 2003.

TECHNICAL FIELD

This invention relates to diazabicyclononane compounds or pharmaceutically acceptable salts thereof, processes for preparing them, pharmaceutical compositions containing them and their use in therapy. The relation relates more particularly to such compounds which are nicotinic acetylcholine receptor agonists.

BACKGROUND OF THE INVENTION

The use of compounds which bind to nicotinic acetylcholine receptors for the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease is discussed in: McDonald et al., (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, Calif.; Williams et al., (1994) "Neuronal Nicotinic Acetylcholine Receptors," Drug News & Perspectives, vol. 7, pp. 205-223; Holladay et al. (1997) J. Med. Chem. 40(26), 4169-4194; Arneric and Brioni (Eds.) (1998) "Neuronal Nicotinic Receptors: Pharmacology and Therapeutic Opportunities", John Wiley & Sons, New York; Levin (Ed.) (2001) "Nicotinic Receptors in the Nervous System" CRC Press.

DESCRIPTION OF THE INVENTION

In one embodiment the present invention encompasses nonane derivatives having activity at nicotonic acetylcholine receptors ("nAChRs"). Nonane derivatives of the invention are those in accord with formula I:

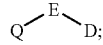

wherein:
Q is a moiety of formula II

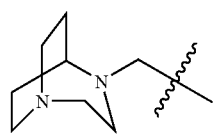

E is selected from $C_1$-$C_6$alkyl, $C_2$-$C_6$alkenyl, $C_3$-$C_6$alkynyl, $C_1$-$C_3$alkoxy$C_1$-$C_3$alkyl, thiazolyl, oxazolyl, imidazolyl, benzothiazolyl, benzoimidazolyl, quinoxalyl, furanyl, thiophenyl, phenyl, naphthyl, pyridyl, bezofuranyl, benzothiophenyl, quinolinyl or a bond, and D is selected from hydrogen, $C_1$-$C_6$alkyl, phenyl, phenylsulphanyl or pyridyl, wherein D may bear 1, 2 or 3 substituents selected from halogen, alkoxy or trifluoromethyl.

In other embodiments the invention encompasses enantiomers, in vivo-hydrolysable precursors and pharmaceutically-acceptable salts of the nonane derivatives, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

Compounds of the invention are ligands for nicotinic acetylcholine receptors (nAChRs) in accord with formula I:

enantionmers and pharmaceutically-acceptable salts thereof, wherein:
Q is a moiety of formula II

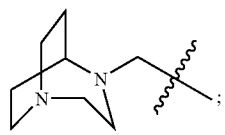

E is selected from $C_1$-$C_6$alkyl, $C_2$-$C_6$alkenyl, $C_2$-$C_6$alkynyl, $C_1$-$C_3$alkoxy$C_1$-$C_3$alkyl, furanyl, thiophenyl, phenyl, naphthyl, pyridyl, bezofuranyl, benzothiophenyl, quinolinyl or a bond, and D is selected from hydrogen, $C_1$-$C_6$alkyl, phenyl, phenylsulphanyl or pyridyl, wherein D may bear 1, 2 or 3 substituents selected from halogen or trifluoromethyl.

Particular compounds of the invention are those in accord with formula I wherein:
E is selected from a bond, $CH_2$—$CH_2$, CH=CH, C≡C, methoxymethyl, furan-2-yl, thiophen-2-yl, thiophen-3-yl, phenyl, naphthyl, pyrid-2-yl, pyrid-3-yl, bezofuran-2-yl, benzothiophen-2-yl, benzothiophen-3-yl, quinolin-2-yl or quinoln-3-yl, and
D is selected from hydrogen, n-pentyl, phenyl, phenylsulphanyl or pyrid-2-yl, wherein D may bear 1, 2 or 3 substituents selected from halogen, alkoxy or trifluoromethyl.

Most particular compounds of the invention are those described herein.

In another aspect the invention relates to compounds according to formula I and their use in therapy and compositions containing them.

In a further aspect the invention relates to compounds according to formula I wherein one or more of the atoms is a radioisotope of the same element. In a particular form of this aspect of the invention the compound of formula I is labelled with tritium. Such radiolabelled compounds is are synthesized either by incorporating radiolabelled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2)

exchange of hydrogen for tritium performed in the presence of tritium gas and a suitable organometallic (e.g. palladium) catalyst.

Compounds of the invention labelled with tritium are useful for the discovery of novel medicinal compounds which bind to and modulate the activity, by agonism, partial agonism, or antagonism, of the α7 nicotinic acetylcholine receptor. Such tritium-labelled compounds may be used in assays that measure the displacement of a such compounds to assess the binding of ligand that bind to α7 nicotinic acetylcholine receptors.

In a particular aspect the invention relates to the use of compounds according to formula I for the therapy of diseases mediated through the action of nicotinic acetylcholine receptors. A more particular aspect of the invention relates to the use of compounds of formula I for the therapy of diseases mediated through the action of α7 nicotinic acetylcholine receptors.

Another aspect of the invention relates to a method of treatment or prophylaxis of human diseases, disorders or conditions in which activation of the α7 nicotinic receptor is beneficial which comprises administering a therapeutically effective amount of a compound of the invention.

Another aspect of the invention relates to a method of treatment or prophylaxis, wherein the disorder is anxiety, schizophrenia or mania or manic depression.

Another aspect of the invention relates to a method of treatment or prophylaxis of neurological disorders, psychotic disorders or intellectual impairment disorders, which comprises administering a therapeutically effective amount of a compound of the invention.

Another aspect of the invention relates to a method of treatment or prophylaxis, wherein the disorder is Alzheimer's disease, learning deficit, cognition deficit, attention deficit, memory loss, or Attention Deficit Hyperactivity Disorder.

Another aspect of the invention relates to a method of treatment or prophylaxis, wherein the disorder is Parkinson's disease, Huntington's disease, Tourette's syndrome, or neurodegenerative disorders in which there is loss of cholinergic synapses.

Another aspect of the invention relates to a method of treatment or prophylaxis of jetlag, cessation of smoking, nicotine addiction, craving, pain, and for ulcerative colitis, which comprises administering a therapeutically effective amount of a compound of the invention.

Another aspect of the invention relates to a pharmaceutical composition comprising a compound of the invention and a pharmaceutically-acceptable diluent or carrier.

A further aspect of the invention relates to a pharmaceutical composition for treating or preventing a condition or disorder mentioned herein arising from dysfunction of nicotinic acetylcholine receptor neurotransmission in a mammal, preferably a human, comprising an amount of a compound of formula I, an enantiomer thereof or a pharmaceutically acceptable salt thereof, effective in treating or preventing such disorder or condition and a pharmaceutically acceptable carrier.

Another aspect of the invention relates to use of the pharmaceutical composition of the invention for the treatment of prophylaxis of human diseases or conditions in which activation of the α7 nicotinic receptor is beneficial.

Another aspect of the invention relates to use of the pharmaceutical composition of the invention for the treatment or prophylaxis of neurological disorders, psychotic disorders or intellectual impairment disorders.

Another aspect of the invention relates to use of the pharmaceutical composition of the invention for the treatment or prophylaxis of Alzheimer's disease, learning deficit, cognition deficit, attention deficit, memory loss, Attention Deficit Hyperactivity Disorder, anxiety, schizophrenia, or mania or manic depression, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, craving, pain, and for ulcerative colitis.

A further aspect of the invention is the use of a compound according to the invention, an enantiomer thereof or a pharmaceutically acceptable salt thereof, in the manufacture of a medicament for the treatment or prophylaxis of the diseases or conditions mentioned herein.

Another aspect of the invention relates to a use of a compound of the invention in the manufacture of a medicament for the treatment or prophylaxis of human diseases, disorders or conditions in which activation of the α7 nicotinic receptor is beneficial.

Another aspect of the invention relates to a use of a compound of the invention in the manufacture of a medicament for the treatment or prophylaxis of neurological disorders, psychotic disorders or intellectual impairment disorders.

Another aspect of the invention relates to the use of a compound of the invention in the manufacture of a medicament for treatment or prophylaxis of Alzheimer's disease, learning deficit, cognition deficit, attention deficit, memory loss or Attention Deficit Hyperactivity Disorder.

Another aspect of the invention relates to the use of a compound of the invention in the manufacture of a medicament for treatment or prophylaxis of anxiety, schizophrenia, or mania or manic depression.

Another aspect of the invention relates to the use of a compound of the invention in the manufacture of a medicament for treatment or prophylaxis of Parkinson's disease, Huntington's disease, Tourette's syndrome, or neurodegenerative disorders in which there is loss of cholinergic synapses.

Another aspect of the invention relates to the use of a compound as described above in the manufacture of a medicament for the treatment or prophylaxis of jet lag, pain, or ulcerative colitis.

Another aspect of the invention relates to the use of a compound of the invention in the manufacture of a medicament for facilitating the cessation of smoking or the treatment of nicotine addiction or craving including that resulting from exposure to products containing nicotine.

For the uses, methods and compositions mentioned herein the dosage administered will, of course, vary with the compound employed, the mode of administration and the treatment desired. However, in general, satisfactory results are obtained when the compounds of the invention are administered at a daily dosage of from about 0.1 mg to about 20 mg/kg of animal body weight. Such doses may be given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or is diluent.

The compounds of formula I, an enantiomer thereof, and pharmaceutically acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically acceptable diluent or carrier.

Examples of diluents and carriers are:
- for tablets and dragees: lactose, starch, talc, stearic acid;
- for capsules: tartaric acid or lactose;
- for injectable solutions: water, alcohols, glycerin, vegetable oils;
- for suppositories: natural or hardened oils or waxes.

There is also provided a process for the preparation of such a pharmaceutical composition which comprises mixing the ingredients.

Compounds according to the invention are agonists of nicotinic acetylcholine receptors. While not being limited by theory, it is believed that agonists of the α7 nAChR (nicotinic acetylcholine receptor) subtype should be useful in the treatment or prophylaxis of neurological disorders, psychotic disorders and intellectual impairment disorders, and have advantages over compounds which are or are also agonists of the α4 nAChR subtype. Therefore, compounds which are selective for the α7 nAChR subtype are preferred. The compounds of the invention are indicated as pharmaceuticals, in particular in the treatment or prophylaxis of neurological disorders, psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, craving, and for the treatment or prophylaxis of nicotine addiction (including that resulting from exposure to products containing nicotine).

It is also believed that compounds according to the invention are useful in the treatment and prophylaxis of ulcerative colitis.

As used herein, the term $C_1$-$C_6$alkyl, $C_1$-$C_6$alkenyl and $C_1$-$C_6$alkynyl refer to a straight-chained, branched, or cyclic forms of such groups.

As used herein the term "halogen" refers to fluorine, chlorine, bromine or iodine.

Methods of Preparation

Methods which may be used for the synthesis of compounds of formula I, include the methods described below.

In the reaction schemes and text that follow E and D are as defined for compounds of formula I and Y is as defined herein.

Scheme 1

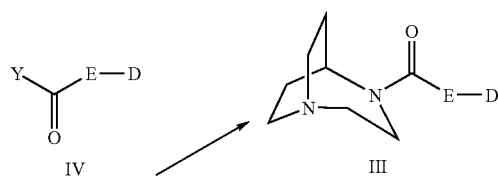

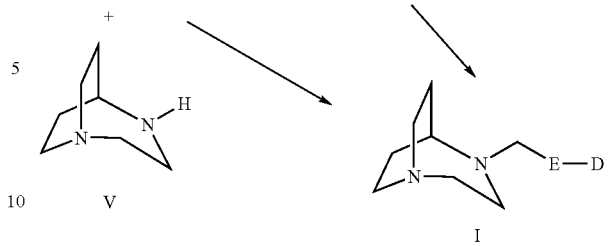

Compounds of formula I may be prepared from compounds of formula III by reaction with an appropriate reducing agent such as diborane or lithium aluminum hydride in a suitable inert solvent at a suitable temperature, generally between −20° C. and the boiling point of the solvent suitable solvents include tetrahydrofuran, diethyl ether, toluene, heptane, or benzene the reaction time will depend inter alia on the solvent and the temperature used, and generally may be up to 24 hours.

Compounds of formula III may be prepared from compounds of formula V by reaction with a compound of formula IV wherein Y represents a suitable leaving group, using a suitable acylation procedure. Suitable leaving groups Y include: OH, halogen, Oalkyl, Oaryl, OCOalkyl, OCOaryl or azide. A suitable acylation procedure involves treatment of a compound of formula V with a compound of formula IV at 0-120° C. in a suitable solvent. The presence of a base, or, when Y=OH, a coupling agent, may also be necessary for the reaction to occur. Suitable bases for the reaction include: 4-(N,N-dimethylamino)pyridine, pyridine, triethylamine, N,N-diisopropylethylamine. The preferred base is N,N-diisopropylethylamine. Suitable coupling agents when Y=OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agent is O-benzotriazol-1-yl-N,N,N',N'-tetramethyluronium tetrafluoroborate. Suitable solvents for the reaction include N,N-dimethylformamide, dimethylsulfoxide, tetrahydrofuran, or chloroform. The preferred solvent is N,N-dimethylformamide. The reaction is preferably performed at a temperature of 0-50° C., and most preferably at a temperature of 20-30° C.

Compounds of formula I may be prepared from compounds of formula V by reaction with a compound of formula IV wherein Y represents hydrogen, by employing a reductive amination method well known to one skilled in the art. See for example: Bhattacharyya, S.; Rana, S.; Gooding, O. W.; Labadie, J. *Tetrahedron Lett.* 2003, 44, 4957 and references therein.

It will be appreciated by those skilled in the art that aromatic substituents in the compounds of the invention, or in intermediates used in the synthesis of compounds of the invention, may be introduced by employing aromatic substitution reactions, functional group transformations to modify existing substituents, or a combination thereof Such reactions may be effected either prior to or immediately following the processes mentioned above. The reagents and reaction conditions for such procedures are known in the art. Specific examples of procedures which may be employed include, but are not limited to, electrophilic functionalisation of an aromatic ring, for example by nitration, halogenation, or acylation; transformation of a nitro group to an amino group, for example by reduction, such as by catalytic hydrogenation; acylation, alkylation, sulfonylation of an amino or hydroxyl group; replacement of an amino group by another functional group by conversion to an intermediate diazonium salt followed by nucleophilic or free radical substitution of the diazonium salt; or replacement of a halogen by another functional group, for example by nucleophilic or organometallically-catalysed substitution reactions.

Where necessary, hydroxy, amino, or other reactive groups may be protected using protecting groups by standard techniques.

The above-described reactions, unless otherwise noted, are usually conducted at a pressure of about one to about three atmospheres, preferably at ambient pressure (about one atmosphere).

Unless otherwise stated, the above-described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

When compounds of formula I exist in tautomeric or enantiomeric forms, all of such forms are included within the scope of the invention. Optical isomers of compounds of the invention may be isolated by separation of a racemic mixture of the compounds using conventional techniques, e.g. fractional crystallisation, or chiral HPLC. Alternatively the individual enantiomers may be made by reaction of the appropriate optically active starting materials under reaction conditions which will not cause racemisation.

Commercial reagents were used without additional purification. Mass spectra were recorded using an HPLC-MS system employing a HP-1100 HPLC and a Micromass LCZ Mass Spectrometer using APCI as the ionization technique, and are reported as m/z for the parent molecular ion. Room temperature or ambient temperature refers to 20-25° C.

The present invention includes by representation, but not by limitation, the following compounds and pharmaceutically-acceptable salts thereof which may be prepared by those skilled in the art using processes and methods analogous to those described herein:

EXAMPLE 1

3-(1,4-diazabicyclo[3.2.2]non-4-yl)-1-phenylpropyne

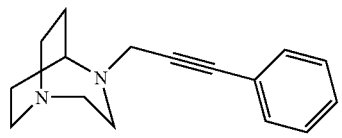

To a stirred mixture of 1,4-diazabicyclo[3.2.2]nonane dihydrochloride (20 mg, 0.10 mmol), MP-Triacetoxyborohydride resin (170. mg, 0.34 mmol) in dry DMF (0.5 mL) at ambient temperature was added phenylpropargyl aldehyde (40 mg, 0.3 mmol). After stirring at ambient temperature for 16 hours the resin was filtered and washed with DMF. The combined filtrate was stirred with MP-TsOH resin (360. mg, 0.5 mmol) for 1 hour, filtered, and washed successively with THF (2×0.5 mL) and MeOH (2×0.5 mL). The amine product was then obtained from the MP-TsOH resin by washing with 2M ammonia in MeOH (3×0.5 mL) and concentrating, and subjected to silica gel chromatography eluting with a chloroform (ammoniated) to 5% methanol/chloroform gradient to give purified title compound as a free base syrup (12.0 mg). MS (ES+) 241 (MH+).

EXAMPLE 2

(1,4-Diazabicyclo[3.2.2]non-4-yl)(5-phenylfuran-2-yl)methane

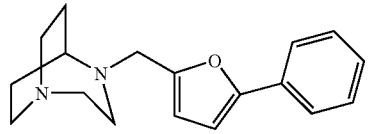

The title compound of the foregoing formula was prepared according to the method of Example 1 using 5-phenyl-2-furaldehyde. MS (ES+) 283 (MH+).

EXAMPLE 3

(1,4-Diazabicyclo[3.2.2]non-4-yl)(biphenyl4-yl)methane

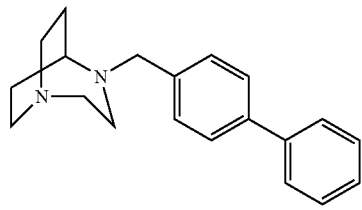

The title compound of the foregoing formula was prepared according to the method of Example 1 using 4-biphenylcarboxaldehyde. MS (ES+) 293 (MH+).

EXAMPLE 4

(1,4-Diazabicyclo[3.2.2]non-4-yl)(5-phenylthiophen-2-yl)methane

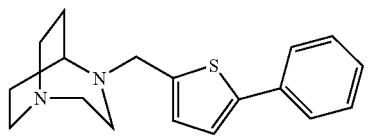

The title compound of the foregoing formula was prepared according to the method of Example 1 using 5-phenyl-2-thiophenecarboxaldehyde. MS (ES+) 299 (MH+).

EXAMPLE 5

(1,4-Diazabicyclo[3.2.2]non-4-yl)(benzofuran-2-yl)methane

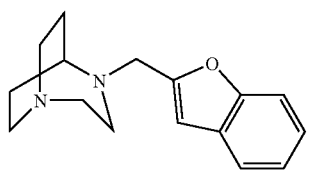

The title compound of the foregoing formula was prepared according to the method of Example 1 using 2-benzofurancarboxaldehyde. MS (ES+) 257 (MH+).

EXAMPLE 6

(1,4-Diazabicyclo[3.2.2]non-4-yl)(naphthalen-2-yl)methane

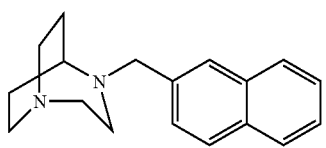

The title compound of the foregoing formula was prepared according to the method of Example 1 using 2-naphthaldehyde. MS (ES+) 267 (MH+).

EXAMPLE 7

3-(1,4-Diazabicyclo[3.2.2]non-4-yl)-1-phenylpropene

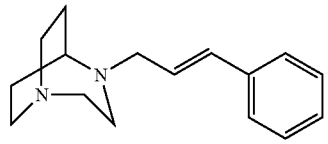

The title compound of the foregoing formula was prepared according to the method of Example 1 using trans-cinnamaldehyde. MS (ES+) 243 (MH+).

EXAMPLE 8

(1,4-Diazabicyclo[3.2.2]non-4-yl)(benzothiophen-3-yl)methane

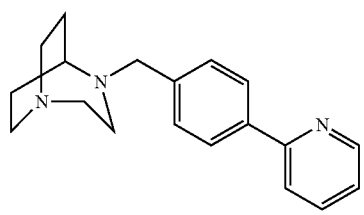

The title compound of the foregoing formula was prepared according to the method of Example 1 using benzothiophene-3-carbaldehyde. MS (ES+) 273 (MH+).

EXAMPLE 9

(1,4-Diazabicyclo[3.2.2]non-4-yl)(4-(2-pyridyl)phenyl)methane

The title compound of the foregoing formula was prepared according to the method of Example 1 using 4-(2-pyridyl)benzaldehyde. MS (ES+) 294 (MH+).

EXAMPLE 10

(1,4-Diazabicyclo[3.2.2]non-4-yl)(6-bromopyridin-2-yl)methane

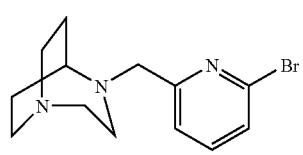

The title compound of the foregoing formula was prepared according to the method of Example 1 using 6-bromopyridine-2-carbaldehyde. MS (ES+) 297 (MH+).

EXAMPLE 11

(1,4-Diazabicyclo[3.2.2]non-4-yl)(quinolin-3-yl)methane

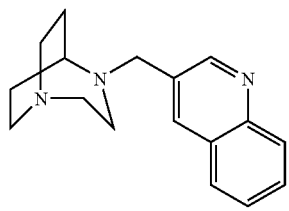

The title compound of the foregoing formula was prepared according to the method of Example 1 using 3-quinolinecarboxaldehyde. MS (ES+) 268 (MH+).

EXAMPLE 12

(1,4-Diazabicyclo[3.2.2]non-4-yl)(quinolin-2-yl)methane

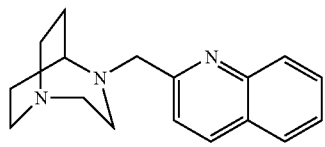

The title compound of the foregoing formula was prepared according to the method of Example 1 using 2-quinolinecarboxaldehyde. MS (ES+) 268 (MH+).

EXAMPLE 13

4-(4-Phenyl-thiophen-2-ylmethyl)-1,4-diaza-bicyclo[3.2.2]nonane

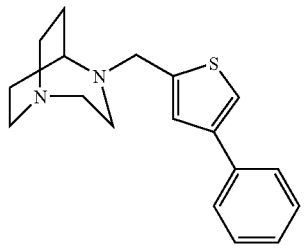

The title compound of the foregoing formula was prepared according to the method of example 1 using 4-phenyl-2-thiophenecarboxaldehyde. MS (ES+) 299 (MH+).

EXAMPLE 14

4-(5-(Pyridin-2-yl)thiophen-2-ylmethyl)-1,4-diazabicyclo[3.2.2]nonane

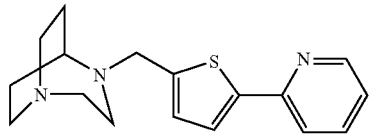

The title compound of the foregoing formula was prepared according to the method of Example 1 using 5-pyridin-2-ylthiophene-2-carbaldehyde. MS (ES+) 300 (MH+).

EXAMPLE 15

4-Biphenyl-3-ymethyl-1,4-diaza-bicyclo[3.2.2]nonane

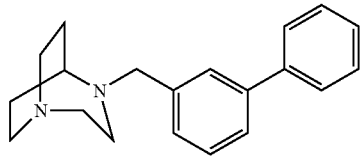

The title compound of the foregoing formula was prepared according to the method of Example 1 using 3-biphenylcarboxaldehyde. MS (ES+) 293 (MH+).

EXAMPLE 16

4-(Pyridin-2-ylmethyl)-1,4-diaza-bicyclo[3.2.2]nonane

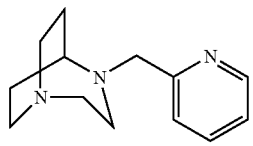

To a stirred solution of 1,4-diazabicyclo[3.2.2]nonane dihydrochloride (120 mg, 0.60 mmol), picolinic acid (85 mg, 0.69 mmol), and diisopropylethylamine (0.45 mL, 2.6 mmol) in dry DMF (2 mL) at ambient temperature was added in succession 1-hydroxybenzotriazole hydrate (85 mg, 0.63 mmol) and TBTU (200 mg, 0.62 mmol). The resulting precipitous mixture was stirred for 12 hours, partitioned between water and chloroform, and extracted with chloroform (3×). The organic layers were combined, washed with water, brine, and dried. The resulting product obtained from concentration of the organic phases was subjected to chromatography on silica gel eluting with a chloroform (ammoniated) to 15% MeOH/chloroform gradient to give (1,4-diazabicyclo[3.2.2]non-4-yl)(pyridin-2-yl)methanone. MS (ES+) 232 (MH+).

To a stirred solution of lithium aluminum hydride (0.33 mL of 1M THF solution) at ambient temperature was added dropwise a solution of (1,4-diazabicyclo[3.2.2]non-4-yl)(pyridin- 2-yl)methanone (120 mg, 0.52 mmol) in dry THF (2 mL). The resulting yellowish solution was stirred for 12 hours, quenched with water and aqueous NaOH, and filtered through diatomaceous earth. The filtrate was concentrated to give the product which was subjected to chromatography on silica gel eluting with an ammoniated-chloroform to 15% MeOH/chloroform gradient to give the title compound as a free base syrup (28.0 mg). MS (ES+) 218 (MH+).

EXAMPLE 17

4-(6- Phenyl-pyridin-2-ylmethyl)-1,4-diaza-bicyclo [3.2.2]nonane

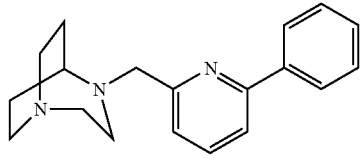

To a stirred solution of 4-(6-bromo-pyridin-2-ylmethyl)-1,4-diaza-bicyclo[3.2.2]nonane (17.0 mg, 0.06 mmol) in a solvent mixture of THF, ethanol, and water (6.0 mL of 1:1:1) was added phenylboronic acid (18 mg, 0.15 mmol), potassium carbonate (70 mg), and a catalytic amount of tetrakis(triphenylphosphine)palladium(0). The mixture was heated at reflux temperature for 3 hours, cooled, and concentrated to near dryness. The residue was triturated with chloroform (3×) and the crude product in chloroform subjected silica gel chromatography eluting with a chloroform (ammoniated) to 5% methanol/chloroform gradient to give the title compound as an off-white solid (4.8 mg). MS (ES+) 294 (MH+).

Other compounds of the invention which may be prepared by the methods described herein include:

4-(3-Phenyl-propyl)-1,4-diaza-bicyclo[3.2.2]nonane having the following formula:

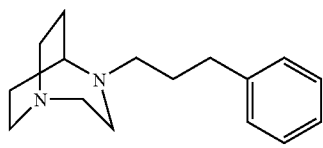

4-Oct-2-ynyl-1,4-diaza-bicyclo[3.2.2]nonane having the following formula:

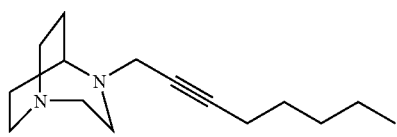

4-(2-Benzyloxy-ethyl)-1,4-diaza-bicyclo[3.2.2]nonane having the following formula:

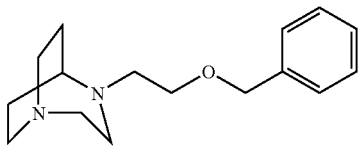

4-(4-Bromo-furan-2-ylmethyl)-1,4-diaza-bicyclo[3.2.2]nonane having the following formula:

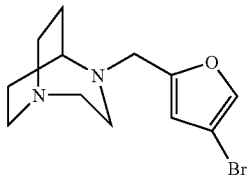

4-[4-(4-Bromo-phenylsulfanyl)-benzyl]-1,4-diaza-bicyclo[3.2.2]nonane having the following formula:

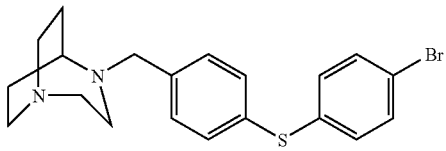

4-(4'-Chloro-biphenyl-4-ylmethyl)-1,4-diaza-bicyclo[3.2.2]nonane having the following formula:

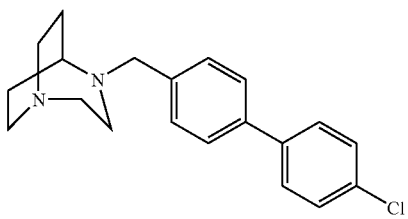

4-(3'-Trifluoromethyl-biphenyl-4-ylmethyl)-1,4-diaza-bicyclo[3.2.2]nonane having the following formula:

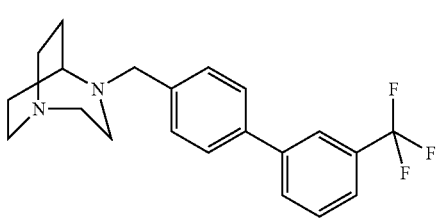

(1,4-Diazabicyclo[3.2.2]non-4-yl)(5-(3-pyridyl)thiophen-2-yl)methane having the following formula:

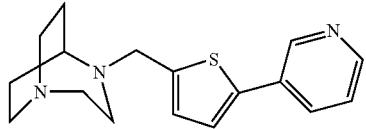

(1,4-Diazabicyclo[3.2.2]non-4-yl)(5-(4-pyridyl)thiophen-2-yl)methane having the following formula:

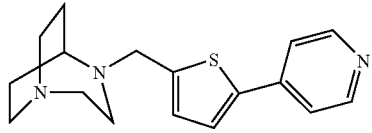

(1,4-Diazabicyclo[3.2.2]non-4-yl)(4-(2-pyridyl)thiophen-2-yl)methane having the following formula:

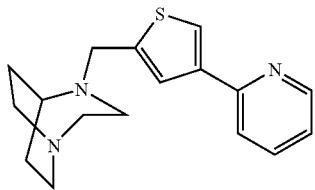

(1,4-Diazabicyclo[3.2.2]non-4-yl)(4-(3-pyridyl)thiophen-2-yl)methane having the following formula:

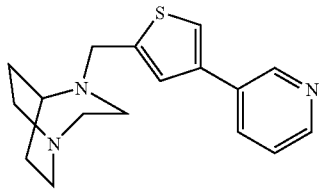

(1,4-Diazabicyclo[3.2.2]non-4-yl)(4-(4-pyridyl)thiophen-2-yl)methane having the following formula:

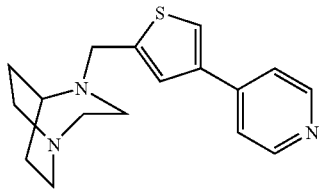

(1,4-Diazabicyclo[3.2.2]non-4-yl)(isoquinolin-3-yl)methane having the following formula:

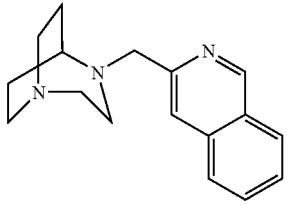

(1,4-Diazabicyclo[3.2.2]non-4-yl)(4-phenylpyridin-2-yl)methane having the following formula:

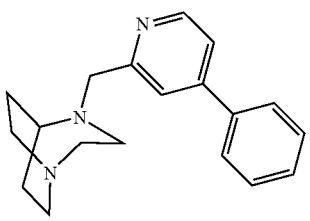

(1,4-Diazabicyclo[3.2.2]non-4-yl)(5-phenylpyridin-2-yl)methane having the following formula:

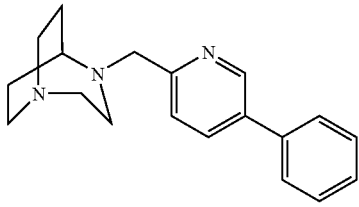

(1,4-Diazabicyclo[3.2.2]non-4-yl)(6-phenylpyridin-2-yl)methane having the following formula:

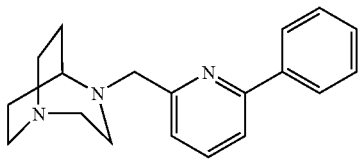

4-(4-Bromo-thiophen-2-ylmethyl)-1,4-diaza-bicyclo[3.2.2]nonane having the following formula:

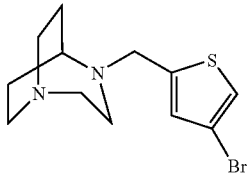

4-(5-Bromo-thiophen-2-ylmethyl)-1,4-diaza-bicyclo[3.2.2]nonane having the following formula:

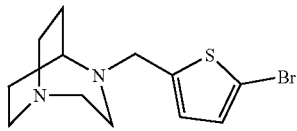

4-(4-(4-Methoxy)phenyl-thiophen-2-ylmethyl)-1,4-diaza-bicyclo[3.2.2]nonane having the following formula:

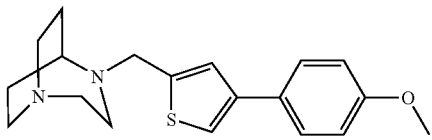

4-(4-(4-Chloro)phenyl-thiophen-2-ylmethyl)-1,4-diaza-bicyclo[3.2.2]nonane having the following formula:

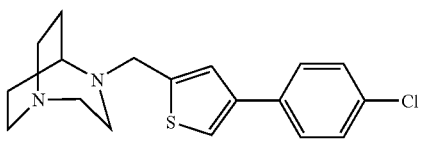

4-(5-(4-Methoxy)phenyl-thiophen-2-ylmethyl)-1,4-diaza-bicyclo[3.2.2]nonane having the following formula:

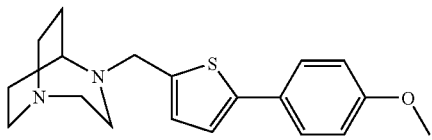

4-(5-(4-Chloro)phenyl-thiophen-2-ylmethyl)-1,4-diaza-bicyclo[3.2.2]nonane having the following formula:

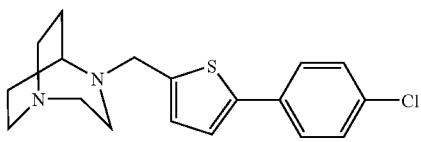

4-(5-(3-Chloro)phenyl-thiophen-2-ylmethyl)-1,4-diaza-bicyclo[3.2.2]nonane having the following formula:

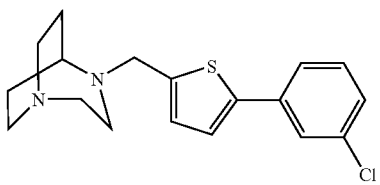

4-(2-Quinoxalin-2-ylmethyl)-1,4-diaza-bicyclo[3.2.2]nonane having the following formula:

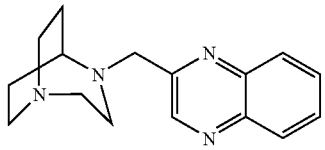

4-(2-Bromo-thiazol-5-ylmethyl)-1,4-diaza-bicyclo[3.2.2]nonane having the following formula:

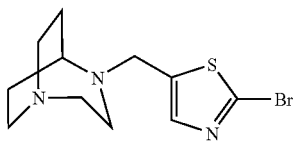

4-Thiazol-5-ylmethyl-1,4-diaza-bicyclo[3.2.2]nonane having the following formula:

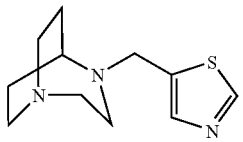

4-(2-Phenyl-thiazol-5-ylmethyl)-1,4-diaza-bicyclo[3.2.2]nonane having the following formula:

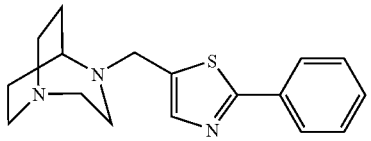

4-(2-Phenyl-imidazol-5-ylmethyl)-1,4-diaza-bicyclo[3.2.2]nonane having the following formula:

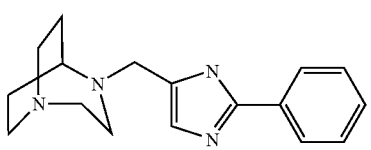

4-(Thiazol-2-ylmethyl)-1,4-diaza-bicyclo[3.2.2]nonane having the following formula:

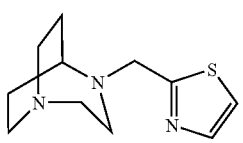

4-(Benzothiazol-2-ylmethyl)-1,4-diaza-bicyclo[3.2.2]nonane having the following formula:

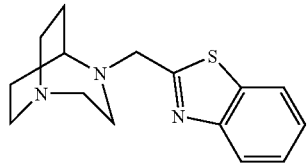

4-(1-Methyl-benzimidazol-2-ylmethyl)-1,4-diaza-bicyclo[3.2.2]nonane having the following formula:

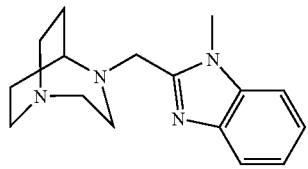

4-(3-Methyl-5-phenyl-thiophen-2-ylmethyl)-1,4-diaza-bicyclo[3.2.2]nonane having the following formula:

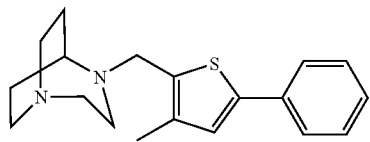

4-(2Phenyl-thiazol-4-ylmethyl)-1,4-diaza-bicyclo[3.2.2]nonane having the following formula:

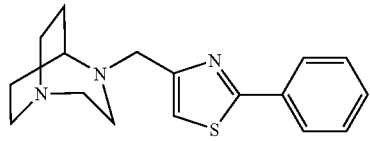

4(4-(3-Bromo-phenyl)thiazol-2-ylmethyl)-1,4-diaza-bicyclo[3.2.2]nonane having the following formula:

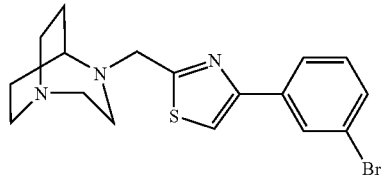

4-(4-Phenyl-thiazol-2-ylmethyl)-1,4-diaza-bicyclo[3.2.2]nonane having the following formula:

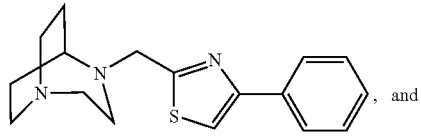, and 4-(4-(Biphen-3-yl)thiazol-2-ylmethyl)-1,4-diaza-bicyclo[3.2.2]nonane having the following formula:

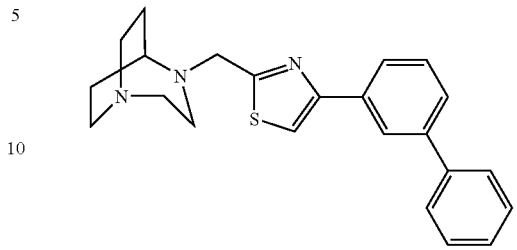

Pharmacology

The pharmacological activity of compounds of the invention may be measured using the tests set out below:

Test A—Assay for Affinity at α7 nAChR Subtype $[^{125}I]$-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30-80 µg) were incubated with 5 nM $[^{125}I]$α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine) in water was critical for low filter blanks (0.07% of total counts per minute). Nonspecific binding was described by 100 µM (−)-nicotine, and specific binding was typically 75%.

Test B—Assay for Affinity to the α4 nAChR Subtype $[^3H]$-(−)-nicotine binding. Using a procedure modified from Martino-Barrows and Kellar (Mol Pharm (1987) 31:169-174), rat brain (cortex and hippocampus) was homogenized as in the $[^{125}I]$α-BTX binding assay, centrifuged for 20 minutes at 12,000×g, washed twice, and then resuspended in HB containing 100 µM diisopropyl fluorophosphate. After 20 minutes at 4° C., membranes (approximately 0.5 mg) were incubated with 3 nM $[^3H]$-(−)-nicotine, test drug, 1 µM atropine, and either 2 mM $CaCl_2$ or 0.5 mM EGTA for 1 h at 4° C., and then filtered over Whatman glass fiber filters (thickness C) (pretreated for 1 h with 0.5% PEI) using a Brandel cell harvester. Nonspecific binding was described by 100 µM carbachol, and specific binding was typically 84%.

Binding Data Analysis for Tests A and B $IC_{50}$ values and pseudo Hill coefficients (nH) were calculated using the non-linear curve-fitting program ALLFIT (DeLean A, Munson P J and Rodbard D (1977) Am. J.

Physiol., 235:E97-E102). Saturation curves were fitted to a one site model, using the non-linear regression program ENZFITTER (Leatherbarrow, R. J. (1987)), yielding KD values of 1.67 and 1.70 nM for the [$^{125}$I]-α-BTX and [3H]-(−)-nicotine ligands respectively. Ki values were estimated using the general Cheng-Prusoff equation:

$$Ki=[IC_{50}]/((2+([ligand]/[KD])n)1/n-1)$$

where a value of n=1 was used whenever nH<1.5 and a value of n=2 was used when nH≧1.5. Samples were assayed in triplicate and were typically ±5%. Ki values were determined using 6 or more drug concentrations. The compounds of the invention are compounds with binding affinities (Ki) of less than 1000 nM in either Test A or Test B, indicating that they are expected to have useful therapeutic activity.

The compounds of the invention have the advantage that they may be less toxic, be more efficacious, be longer acting, have a broader range of activity, be more potent, produce fewer side effects, are more easily absorbed or have other useful pharmacological properties.

What is claimed is:

1. A compound in accord with formula I:

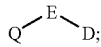

enantiomers and pharmaceutically-acceptable salts thereof, wherein:

Q is a moiety of formula II

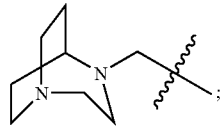

E is selected from thiazolyl, imidazolyl, and

D is selected from hydrogen, $C_1$-$C_6$alkyl, phenyl, phenylsulphanyl or pyridyl, wherein D may have 1, 2 or 3 substituents selected from halogen, alkoxy or trifluoromethyl.

2. A compound according to claim 1, wherein:

D is selected from hydrogen, n-pentyl, phenyl, phenylsulphanyl or pyrid-2-yl, wherein D may have 1, 2 or 3 substituents selected from halogen, alkoxy or trifluoromethyl.

3. A compound according to claim 1, selected from:
4-(thiazol-5-ylmethyl)-1,4-diaza-bicyclo[3.2.2]nonane;
4-(2-phenyl-thiazol-5-ylmethyl)-1,4-diaza-bicyclo[3.2.2]nonane;
4-(2-phenyl-imidazol-5-ylmethyl)-1,4-diaza-bicyclo[3.2.2]nonane;
4-(thiazol-2-ylmethyl)-1,4-diaza-bicyclo[3.2.2]nonane;
4-(2-phenyl-thiazol-4-ylmethyl)-1,4-diaza-bicyclo[3.2.2]nonane; and
4-(4-phenyl-thiazol-2-ylmethyl)-1,4-diaza-bicyclo[3.2.2]nonane.

4. A pharmaceutical composition comprising a compound according to claim 1 and a pharmaceutically-acceptable diluent or carrier.

* * * * *